US007265822B2

(12) United States Patent
Schmitt

(10) Patent No.: US 7,265,822 B2
(45) Date of Patent: Sep. 4, 2007

(54) METHOD AND APPARATUS FOR DETERMINING PRESENCE OF A COMPONENT IN A PRINTED CIRCUIT BOARD

(75) Inventor: Kevin Schmitt, Hoffman Estates, IL (US)

(73) Assignee: Test Coach Corporation, Hoffman Estates, IL (US)

( * ) Notice: Subject to any disclaimer, the term of this patent is extended or adjusted under 35 U.S.C. 154(b) by 266 days.

(21) Appl. No.: 10/956,711

(22) Filed: Oct. 1, 2004

(65) Prior Publication Data
US 2006/0072116 A1 Apr. 6, 2006

(51) Int. Cl.
G01N 21/00 (2006.01)
G01J 3/46 (2006.01)

(52) U.S. Cl. .................... 356/237.1; 356/402; 356/612
(58) Field of Classification Search ............. 356/237.1
See application file for complete search history.

(56) References Cited

U.S. PATENT DOCUMENTS

| 1,971,317 | A | * | 8/1934 | Horton et al. .............. 356/425 |
| 4,549,206 | A | * | 10/1985 | Suzuki et al. .............. 348/126 |
| 4,611,116 | A | * | 9/1986 | Batt .......................... 250/239 |
| 4,681,454 | A |   | 7/1987 | Breemer |
| 4,775,640 | A | * | 10/1988 | Chan ......................... 438/16 |
| 4,808,815 | A |   | 2/1989 | Langley |
| 5,065,007 | A |   | 11/1991 | Tanaka |
| 5,078,497 | A | * | 1/1992 | Borton et al. .............. 356/446 |
| 5,245,421 | A | * | 9/1993 | Robertson et al. .......... 348/126 |
| 5,381,103 | A |   | 1/1995 | Edmond et al. |
| 5,568,267 | A |   | 10/1996 | Sunamori et al. |
| 5,686,994 | A | * | 11/1997 | Tokura ....................... 348/126 |
| 5,760,893 | A | * | 6/1998 | Raymond ................. 356/237.1 |
| 5,963,333 | A | * | 10/1999 | Walowit et al. ............ 356/425 |
| 6,084,663 | A | * | 7/2000 | Seng ....................... 356/237.4 |
| 6,127,783 | A |   | 10/2000 | Pashley et al. |
| 6,172,745 | B1 | * | 1/2001 | Voser et al. ................ 356/71 |
| 6,480,394 | B1 | * | 11/2002 | Feld et al. ................. 361/760 |
| 6,490,037 | B1 |   | 12/2002 | Schmitt |
| 2001/0012107 | A1 | * | 8/2001 | Toh ........................... 356/601 |

FOREIGN PATENT DOCUMENTS

| EP | 0 285 493 A2 | 10/1988 |
| GB | 2 364 118 A | 1/2002 |
| JP | 03-133183 | 6/1991 |
| JP | 2000-223746 | 8/2000 |

OTHER PUBLICATIONS

Merriam-Webster Online Dictionary (n.d.). Retrieved Sep. 14, 2006, from http://www.m-w.com/dictionary/window.*
Programmable Color Light-to Frequency Converter (specification sheet), *Texas Advanced Optoelectronic Solutions Inc.*, pp. 1-9, Feb. 2003.

* cited by examiner

Primary Examiner—Layla G. Lauchman
Assistant Examiner—Jonathan Skovholt
(74) Attorney, Agent, or Firm—Pauley Petersen & Erickson

(57) ABSTRACT

A method and apparatus for determining color, presence and/or polarity of a component in a printed circuit board includes a sensor and an LED positioned behind a faceplate. The faceplate abuts the component and light is reflected from the LED off the component and received by the sensor. A resulting output signal is analyzed to determine the color, presence and/or polarity of the component in the printed circuit board, thereby ensuring that the printed circuit board is correctly assembled.

14 Claims, 2 Drawing Sheets

METHOD AND APPARATUS FOR DETERMINING PRESENCE OF A COMPONENT IN A PRINTED CIRCUIT BOARD

BACKGROUND OF THE INVENTION

1. Field of the Invention

This invention relates to a method and apparatus for testing for the presence, polarity and/or color of a component in a printed circuit board.

2. Description of Related Art

Printed circuit boards typically contain multiple components including: light emitting diodes (LEDs); resistors, capacitors, processors and similar such components. Typically, verification of the presence of such components in a printed circuit board required powering up a fully rendered printed circuit board and manually verifying the presence of the correct components. Alternatively, a test fixture may be constructed including bulky and expensive fiber optics that extend between the printed circuit board to be tested and a test system.

Verification of the presence and operation of LEDs within a printed circuit board may be accomplished without a power supply such as described in U.S. Pat. No. 6,490,037, issued to Schmitt, which is hereby incorporated by reference in its entirety in a manner consistent with the present document

SUMMARY OF THE INVENTION

A method and apparatus for determination of presence, polarity and/or color of a component in a printed circuit board according to a preferred embodiment of this invention eliminates much of the time-consuming and costly procedures required by manual determination and the equally costly test fixtures requiring time-intensive and complex set-up and calibration.

The apparatus according to a preferred embodiment of this invention preferably includes a device, termed a P-FNN™ device, that includes both a light emitting diode light source, hereinafter an LED, and a sensor in a simple, easy to mount assembly. The device for determining at least one of a presence, an orientation and a color of a component in printed circuit board preferably includes the LED and the sensor arranged within a housing or similar structure. The housing preferably includes a faceplate that extends at least partially over an end surface of device and may include a window formed within the faceplate.

The sensor and the LED are preferably positioned beneath the faceplate and, more preferably, directly beneath the window. As such, the LED positioned adjacent to the sensor such that, in an illuminated condition, the LED emits light from the window of device which is then reflected off the component and back to the sensor.

An output probe is preferably connected with respect to the sensor and provides an output signal proportional to light reflected from the component. Additional probes may also be connected with respect to the device. At least one and preferably all such probes are spring-loaded to permit direct contact and/or engagement of the faceplate with a surface of the component.

Accordingly, a method for testing for the presence, color and/or polarity of the component may include biasing the device against a respective component for testing then illuminating the LED within the device and through the window of the faceplate. An amount of light is reflected off the component and back to the sensor. Based upon the reading from the sensor, an output signal, preferably in the form of an output voltage, is delivered from the sensor to an output device such as a microprocessor to determine the presence, color and/or polarity of the respective component. A pass-fail signal may then be generated by the output device to indicate the presence or absence of an erroneous component or erroneous placement of a correct component.

BRIEF DESCRIPTION OF THE DRAWINGS

The above-mentioned and other features and objects of this invention will be better understood from the following detailed description taken in conjunction with the drawings wherein.

DESCRIPTION OF PREFERRED EMBODIMENTS

Figure 1:
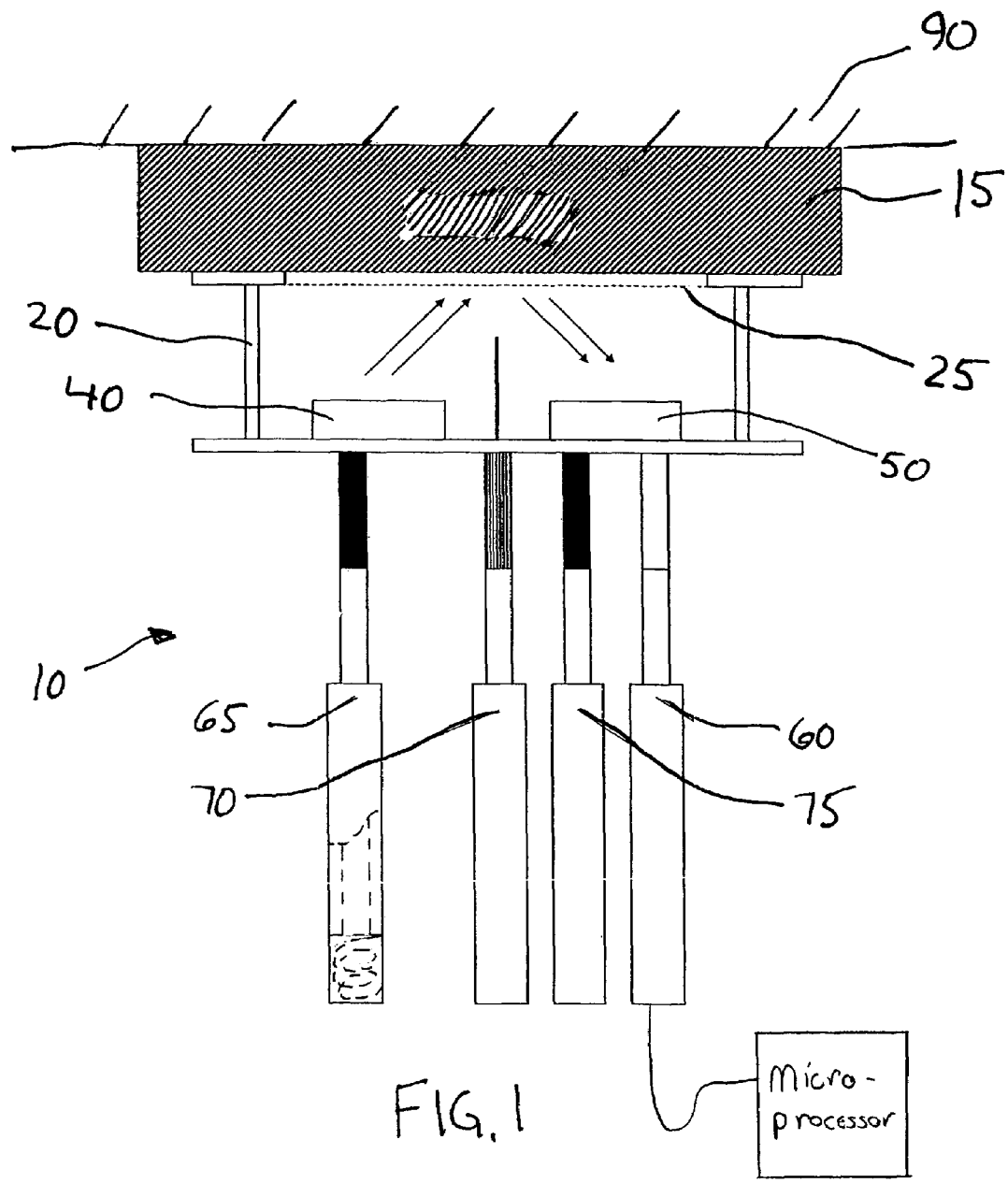
FIG. 1 is a schematic front view of a device according to one preferred embodiment of this invention.
Figure 2:
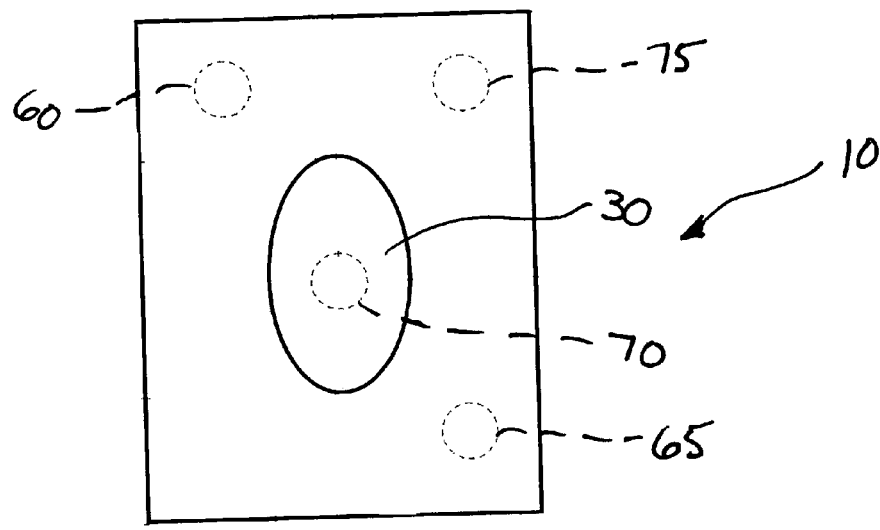
FIG. 2 is a schematic top view of the device shown in FIG. 1.
Figure 3:
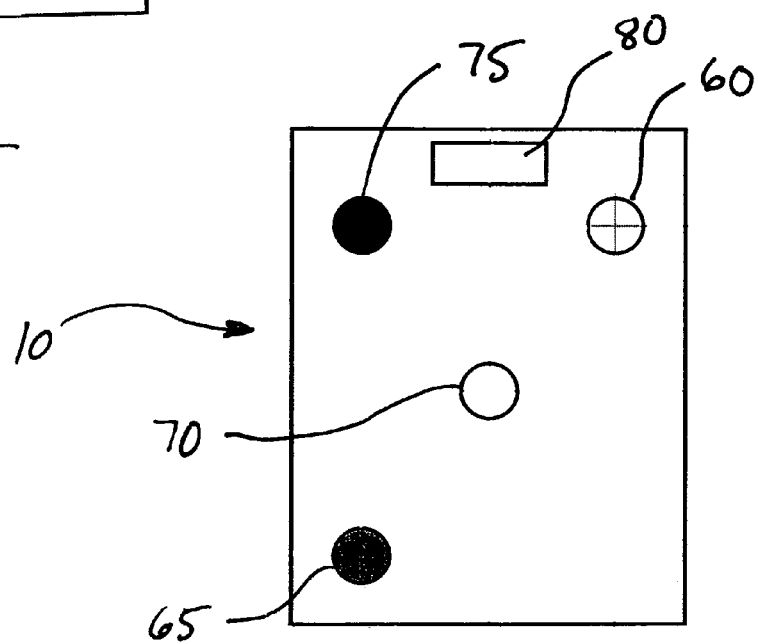
FIG. 3 is a schematic bottom view of the device shown in FIG. 1.

According to one preferred embodiment of this invention, an apparatus and system for determining a presence and/or orientation and/or color of a component 15 in printed circuit board 90 is shown in FIGS. 1-3. Components 15 are typically used in printed circuit boards 90 and require verification and determination of their presence, orientation and/or color for confirmation of the correct operation and set-up of printed circuit board 90. Such components 15 may include, capacitors that require correct polarity for operation and similar such components.

The subject invention is a cost effective method of identifying object presence, orientation, and/or color. The subject invention includes device 10, termed a P-FINN™ device, that includes both a light emitting diode light source, hereinafter LED 40, and sensor 50 in a simple, easy to mount assembly. Device 10 is preferably available with blue, green or red light sources depending upon the characteristics of component 15 to be detected. The intensity of the reflected light is related to the color of the object. An output signal from device 10 is thus proportional to the reflected light.

An apparatus or device 10 for determining at least one of a presence, an orientation and a color of a component in printed circuit board 90 preferably includes LED 40 and sensor 50 arranged within housing 20 or similar structure.

Housing 20 preferably includes faceplate 25 that extends at least partially over an end surface of device 10. Faceplate 25 is preferably formed of a material the same or similar to printed circuit board substrate. According to a preferred embodiment of this invention faceplate 25 further includes window 30 formed within faceplate 25.

As briefly described above, sensor 50 and LED 40 are preferably positioned beneath faceplate 25 and, more preferably, directly beneath window 30 within faceplate 25. Faceplate 25 is preferably black to provide a shrouding effect with respect to ambient light and other potential interference among LED 40, sensor 50 and component 15.

LED 40 is preferably positioned adjacent to sensor 50 such that, in an illuminated condition, LED 40 emits light from window 30 of device 10 which is reflected off component 15 back to sensor 50.

Output probe 60 is preferably connected with respect to sensor 50 and provides an output signal proportional to light reflected from component 15. An output device (not shown) is preferably connected with respect to output probe 60 to indicate a pass-fail condition based on the output signal. That is, the output device preferably indicates whether component 15 is present and/or correctly colored and/or correctly marked and/or correctly oriented.

In addition, device 10 preferably includes input probe 75 connected with respect to sensor 50 and providing power to sensor 50. Device 10 also preferably includes ground probe 65 connected between device 10 and a ground.

According to one preferred embodiment of this invention, device 10 further includes central probe 70. Central probe 70 is preferably connected with respect to device 10, such as relative to housing 20 and/or faceplate 25 and may be used for aligning LED 40 and sensor 50 relative to component 15. More specifically, central probe 70 may be directly aligned with window 30 in faceplate 25 to provide indicia of how to center device 10 over component 15.

According to a preferred embodiment of this invention, at least one and preferably all of probes 60, 65, 70, 75 are spring-loaded to permit direct contact and/or engagement of faceplate 25 with a surface of component 15. Probes 60, 65, 70, 75 may include an internal spring for biasing device 10 against component 15. Therefore, at least one probe 60, 65, 70, 75 connected with respect to sensor 50 act to bias sensor 50 and/or faceplate 25 against component 15 so that light from LED 40 is accurately reflected off component 15 and back to sensor 50.

Faceplate 25 is preferably sized to include a thickness that maintains a required focal distance between LED 40/sensor 50 and component 15. According to the described invention, as component 15 being tested moves further away from focal point of sensor 50, the intensity of the reflected light is rapidly diminished. Component 15 being tested preferably touches faceplate 25. Sensor 50 is therefore preferably bias mounted on spring loaded probes and can be slightly compressed to insure that component 15 is touching faceplate 25. A microprocessor may be connected with respect to sensor 50 and/or output probe 60 for calculating the presence, color and/or orientation of component 15.

Accordingly, a method for testing for the presence, color and/or polarity of component 15 on a printed circuit board 90 may include the following. Initially, printed circuit 90 board may be mounted in a suitable test fixture (not shown) to enable analysis. The test fixture may include one or more devices 10 that are then preferably positioned relative to each component 15 to be tested within printed circuit board 90. Next each device 10 is biased against a respective component 15 for testing. As herein described, faceplate 25 may comprise a suitable thickness to provide a proper focal distance from component 15.

LED 40 is then illuminated within device 10 and through window 30 of faceplate 25. An amount of light is reflected off component 15 and back to sensor 50. Based upon the reading from sensor 50 and output signal, preferably in the form of an output voltage. The output signal is delivered from sensor 50 and to an output device such as a microprocessor to determine the presence, color and/or polarity of the respective component 15.

Device 10 preferably operates by reflecting light from LED 40 to a focal point and back to sensor 50. The output of sensor 50 is preferably a DC voltage proportional to the reflective light. The more light reflected the higher the DC output voltage. LED 40 and sensor 50 may be available in a package such as those manufactured by TAOS Inc. of Plano, Tex., part number TRS1722, 1755 and 1766.

In an environment requiring testing for presence of component 15, light would reflect off of component 15, such as a capacitor, and back into sensor 50 resulting in a high output voltage. If component 15 is missing, light would not reflect back and would result in a low output voltage.

In the opposite situation, if component 15 was black and non reflective, a reflective surface behind component could be used to reflect the light back if component 15 is missing. For example, if a black component 15 was mounted on a green printed circuit board, device 10 having a green LED 40 could be used and a high voltage out would indicate a failure.

According to another preferred use of the subject invention, the orientation or polarity of component 15 may be verified. In such an orientation application, component 15 preferably includes a non-symmetrical color pattern. For example, if component is light in color and has a black orientation mark, device 10 would be aligned to a location so the focal point is either the dark non-reflective orientation mark or the reflective surface under sensor 50. Preferably, device 10 is aligned using the smaller of the two indicia. Preferably, the sensor's DC output will be low if targeting the dark orientation mark. Accordingly, the sensor's DC output would be high if it was targeted at the lighter reflective surface. Typically, if component 15 is missing the output signal would be near zero.

According to a preferred operation of this invention requiring verification of color of component 15, the amount of reflective light is proportional to the relationship between the color of the light and the color of component 15 that the light is reflecting off. For this reason, device 10 may include one of three different models having differently colored LEDs 40, blue, green and red, depending upon desired operation.

According to a preferred embodiment of this invention, a plurality of devices 10 may be used to test a fully rendered printed circuit board 90 containing a plurality of components 15 for testing.

Other than a power and ground connection, the only other preferred connection to sensor 50 is the output. LED 40 will light up when power is applied from a power source to input probe 75 and ground probe 70. Optionally, device may further include an LED bias pin used to fine tune the LED's intensity.

According to one preferred embodiment of this invention, operating features of device 10 may include: an operating voltage from approximately 3.0 Vdc to 5.5 Vdc; "bed of nails" style probes 60, 65, 70, 75 used for connections; placement and/or orientation determined with one signal measurement; right angle mounting for simplified installation; totally automated testing with no operator action required; operation significantly faster than operator inspection; and/or optional bias for fine tuning the intensity of LED 40.

According to a preferred embodiment of this invention, suitable applications may include: any test environment where placement test is required; a broad range of industries such as, automotive, telecommunication, network solutions and medical; quality control for most in-line manufacturing environments; polarized component or capacitor polarity testing; placement testing of many components on a PCB assembly that cannot be electrically verified.

As described briefly above, sensor 50 alignment and distance is an important aspect of the subject invention. The focal point of sensor 50 is generally centered directly under window 30 above sensor 50. Device 10, specifically faceplate 25, preferably touches component 15 under test for optimal operation. The targeted location on component should be centered in window 30 of device 10. Central probe 70 of device 10 preferably corresponds with the optical center of device 10 but may not be the physical center.

Device 10 having a blue LED is recommended for most applications. For components having green/yellow color, black color and/or non-clear coating, a green LED is recommended within device 10. For components 15 having red/orange color, black color and/or non-clear coatings, a red LED is recommended within device 10. For most other application, a blue LED is recommended within device 10.

Device 10 may further include internal resistor 80 used to bias LED 40. Resistor 80 is preferably connected between input probe 75 and central probe 70. At 5V operation this supplies approximately 1-5 mA of the maximum 30 mA that LED 40 is rated for. The optional central probe 70 can be used to adjust the LED's light in the following ways: (1) to increase the intensity of the light, a parallel resistor from central probe 70 to the input probe 75 can be added (the minimum combined resistance is preferably greater than 100 ohms); or (2) to decrease the intensity of the light a load resistor can be placed between central probe 70 and ground probe 65.

A DC voltage may be applied to central probe 70 with reference to ground probe 65 according the chart below. Such voltage will be directly across LED 40 and is preferably current limited with a series resistor.

---
BLUE sensor from 2.2 V to a maximum of 3.0 V
GREEN sensor from 2.3 V to a maximum of 3.0 V
RED sensor from 2.7 V to a maximum of 3.0 V
---

According to a preferred embodiment of this invention, the properties of device 10 are preferably as follows. Dimensions of device 10 are preferably 0.380 inch×0.235 inch×0.150 inch, not including probes. Device 10 requires a minimal power voltage source, which may vary from approximately 3.0 volts to approximately 5.5 volts, where current is typically 10 mA@5V. Input probe 75 is preferably marked with a red heat-shrink on the lead. Ground probe 65 is preferably marked with a black heat-shrink on the lead. Output probe 60 is preferably marked with a clear heat-shrink on the lead. Central probe 70, if desired, is preferably marked with a colored heat shrink to indicate the color of the respective LED 40 within device 10.

According to a preferred embodiment of this invention, a recommended test flows includes: (a) turn on power to device 10; (b) if applicable, adjust LED 40 brightness using central probe 70; and (c) measure voltage in the output signal from output probe 60.

Outside light from sources other than component 15 being tested should be prevented from reaching surface of sensor 15 while making measurements. As component 15 under test moves further away from focal point of sensor 50, the intensity of the reflected light is rapidly diminished. Component 15 under test preferably touches faceplate 25 or intensity should be increased using the bias pin.

After mechanical installation of device 10, it should be verified for proper operation before use in production. One simple step in this process may be to measure the diode drop from the central probe 70 to ground probe 65 and also verify that LED 40 lights up.

The DC output voltage should also be checked to insure that there is enough difference when light is reflected back into sensor 50 and when it is not. After this is accomplished the test's voltage limits can be determined to either pass or fail component 15. The easiest way to do this is to check the limits with component 15 placed and orientated properly and with it absent or reversed. If the DC output voltage difference is not large enough to detect a fault, central probe 70 of device 10 may be used to change the intensity of LED 40 or another device 10 having a differently colored internal LED 40 maybe better suited for the test surface. According to a preferred embodiment of this invention, it is also important to check to insure contact between faceplate 25 and component 15.

Preferred wiring of device 10 includes: red (Power) to Vdd (switched 5V typical); black (GND) to ground (OV ref); clear (Output) output to measurement device or switch matrix N/A (Bias).

While in the foregoing specification this invention has been described in relation to certain preferred embodiments thereof, and many details have been set forth for purpose of illustration, it will be apparent to those skilled in the art that the method and apparatus according to this invention are susceptible to additional embodiments and that certain of the details described herein can be varied considerably without departing from the basic principles of the invention.

I claim:

1. An apparatus for determining at least one of a presence, an orientation and a color of a component in a printed circuit board, the apparatus comprising:
    a sensor;
    a faceplate positioned over the sensor and abutting the component, the faceplate having a window and a thickness that maintains a focal distance of the sensor;
    a Light Emitting Diode (LED) positioned adjacent to the sensor such that in an illuminated condition, the LED emits light from the window and off the component;
    an output probe connected to the sensor, the output probe providing an output signal proportional to light reflected from the component, wherein the output probe is spring-loaded to engage the faceplate with the component; and
    an output device connected with respect to the output probe to indicate a pass-fail condition based on the output signal.

2. The apparatus of claim 1 further comprising:
    an input probe connected to the sensor, the input probe providing power to the sensor; and
    a ground probe connected to the sensor.

3. The apparatus of claim 1 further comprising:
    a microprocessor connected with respect to the sensor and the output probe for calculating the presence of the component.

4. The apparatus of claim 1 further comprising:
    a central probe connected with respect to the faceplate, the central probe for aligning the LED and the sensor relative to the component.

5. The apparatus of claim 1 wherein the faceplate is black.

6. An apparatus for determining the presence of a component in a printed circuit board, the apparatus comprising:
    a housing with a faceplate having a window;
    a sensor disposed within the housing;
    a Light Emitting Diode (LED) disposed within the housing, the faceplate positioned over the sensor and the LED, and the faceplate directly contacting a surface of the component;
    at least one probe connected with respect to the sensor, the at least one probe having an internal spring biasing the sensor against the component so that light from the LED is reflected off the component, through the window and back to the sensor.

7. The apparatus of claim 6 further comprising:
a central probe connected with respect to the faceplate, the central probe aligned with the window.

8. The apparatus of claim 6 further comprising:
an input probe connected with respect to the sensor, the input probe providing power to the sensor; and
a ground probe connected between the sensor and a ground.

9. The apparatus of claim 6 further comprising:
a central probe connected with respect to at least one of the sensor and the LED, the central probe for aligning the LED and the sensor relative to the component.

10. A method for testing for at least one of a presence, a color and a polarity of a component on a printed circuit board, the method comprising:
positioning a device having a sensor, a faceplate over the sensor, a Light Emitting Diode (LED) and at least one spring-loaded probe against a surface of the component, the LED with the faceplate having a thickness that maintains a focal distance of the sensor;
spacing the sensor from the component a predetermined focal distance using a thickness of the faceplate;
biasing the faceplate against the component using the at least one spring-loaded probe connected with respect to the device;
illuminating the LED to reflect an amount of light off the component and back to the sensor;
sending an output signal from the sensor; and
determining at least one of a presence, a color and a polarity of the component with a microprocessor connected to the device; and providing the determination to an output device 11. The method of claim 10 further comprising:
providing a window in the faceplate.

12. The method of claim 11 further comprising:
connecting a central probe with the device; and
aligning the central probe with the window of the faceplate.

13. The method of claim 10 further comprising:
providing a plurality of devices against a plurality of respective components to test an assembled printed circuit board.

14. The method of claim 10 further comprising:
biasing the device against the component using at least one probe connected with respect to the device.

* * * * *